United States Patent
Sun et al.

(10) Patent No.: US 8,050,872 B2
(45) Date of Patent: Nov. 1, 2011

(54) SYSTEM AND METHOD FOR RAPID SEARCHING OF HIGHLY SIMILAR PROTEIN-CODING SEQUENCES USING BIPARTITE GRAPH MATCHING

(75) Inventors: Bing Sun, Jersey City, NJ (US); Jacob T. Schwartz, New York, NY (US); Ofer H. Gill, Springfield, NJ (US); Bhubaneswar Mishra, Great Neck, NY (US)

(73) Assignee: New York University, New York, NY (US)

( * ) Notice: Subject to any disclaimer, the term of this patent is extended or adjusted under 35 U.S.C. 154(b) by 819 days.

(21) Appl. No.: 12/115,187

(22) Filed: May 5, 2008

(65) Prior Publication Data

US 2009/0124507 A1 May 14, 2009

Related U.S. Application Data

(60) Provisional application No. 60/916,034, filed on May 4, 2007.

(51) Int. Cl.
*G06F 15/00* (2006.01)
*G06F 19/00* (2011.01)
*G11C 17/00* (2006.01)

(52) U.S. Cl. .............................. 702/20; 700/1; 365/94

(58) Field of Classification Search .................. None
See application file for complete search history.

(56) References Cited

U.S. PATENT DOCUMENTS

2005/0159898 A1* 7/2005 Yasuda et al. ................... 702/20

OTHER PUBLICATIONS

Liao et al. The UniMarker (UM) method for synteny mapping of large genomes Bioinformatics vol. 20, pp. 3156-3165 (2004).*
McVitie et al. The Stable Marriage Problem Communications of the ACM vol. 14, pp. 486-490 (1971).*

* cited by examiner

*Primary Examiner* — John S Brusca
(74) *Attorney, Agent, or Firm* — Dorsey & Whitney LLP

(57) ABSTRACT

An exemplary embodiment of system, computer-accessible medium and method for comparing a first genome to a second genome. For example, a first genome may be compared to a second genome by building a first library for the first genome and a second library for the second genome, providing a plurality of matches between elements in the first library common to elements in the second library, ranking each match to determine a likelihood of similarity between the common elements in the first and second libraries; and associating matches having a predetermined likelihood. The association may be performed efficiently by a stable marriage procedure.

41 Claims, 5 Drawing Sheets

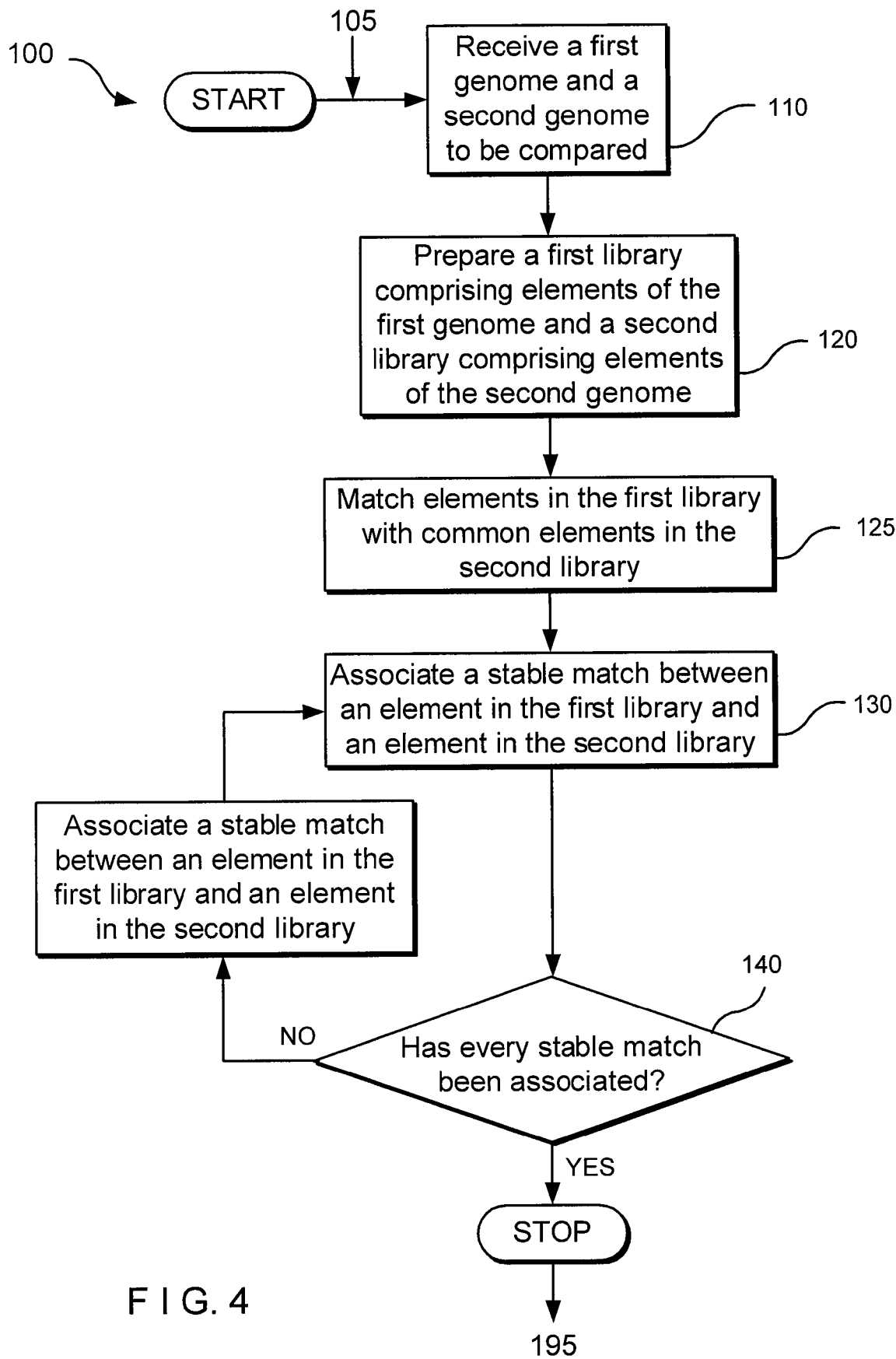
F I G. 4

SYSTEM AND METHOD FOR RAPID SEARCHING OF HIGHLY SIMILAR PROTEIN-CODING SEQUENCES USING BIPARTITE GRAPH MATCHING

CROSS-REFERENCE TO RELATED APPLICATION(S)

This application claims priority from 35 U.S.C. §119(e) to U.S. Provisional Patent Application No. 60/916,034, filed May 4, 2007, which is hereby incorporated by reference in its entirety.

GOVERNMENTAL SUPPORT

The research leading to the present invention was supported, at least in part, by the Department of the Army under Award Number W81XWH-04-1-0307. Thus, the U.S. government may have certain rights in the invention.

BACKGROUND INFORMATION

In the past decade, many genome projects have produced complete genomes for increasingly many organisms. Since 1999 many tools have proven effective in aligning large genomic sequences of two closely related organisms. Such tools include: MUMmer, which is described, e.g., in Delcher et al., "Alignment of whole genomes," *Nucleic Acids Res.*, pages 2369-2376 (1999); GLASS, which is described, e.g., in Pachter et al., "Human and mouse gene structure: Comparative analysis and application to exon prediction," *Genome Res.*, pages 50-958 (2000); AVID, which is described, e.g., in Bray et al., "Avid: A global alignment program," *Genome Res.*, pages 97-102 (2003); DIALIGN, which is described, e.g., in Morgenstern et al., "Exon discovery by genomic sequence alignment," *Bioinformatics*, (6):777-787 (2002); LAGAN, which is described, e.g., in Brudno et al., "Lagan and multi-lagan: Efficient tools for large-scale multiple alignment of genomic dna," *Genome Res.*, pages 721-731 (2003); BLASTZ, which is described, e.g., in Schwartz et al., "Human-mouse alignments with blastz," *Genome Res.*, page 103-107 (2003); and BLAT, which is described, e.g., in Kent, "Blat—the blast-like alignment tool," *Genome Res.*, (4):656-664 (2002).

Characteristics common to many of these programs include: (i) an assumption that conserved regions of the sequences being aligned appear in the same order and orientation, which may be particularly likely for closely related organisms; (ii) the construction of tables of scores for matches and mismatches between amino acids or nucleotides, which may incorporate penalties for insertions or deletions, and which may be used to obtain mathematically 'optimal' alignments; and (iii) the search for exact or spaced exact matches (e.g., in local alignment programs), and the extension of local similarities in both directions in passes directed by specified scoring functions.

However, certain shortcomings may limit the use of many of these programs. First, genomic order and orientation may not be conserved between species of interest. Second, the scoring matrix (e.g., a PAM or a BLOSUM matrix) which may be most appropriate for aligning a set of sequences should preferably be determined by the level of relatedness of sequences. Hence, a pre-estimate of a percentage of similarity between two genomes may be required to choose a proper scoring matrix. Third, a variation in the rate of evolution across the genome can make it impractical to pick a universal scoring matrix or a set of gap costs as described, e.g., in Frazer et al., "Cross-species sequence comparisons: A review of methods and available resources," *Genome Res.*, pages 1-12 (2003). Finally, when using a "match and extend" strategy, many local procedures can pay a steep cost in extending short matches in both directions.

Thus, comparing vertebrate genomes can require efficient cross-species sequence alignment programs. It may be desirable to have a system and method for cross-species genome alignment which reduces the above-mentioned deficiencies.

SUMMARY OF EXEMPLARY EMBODIMENTS OF THE INVENTION

A novel mer-based system and method (Clean Ordered Mer-Based Alignment Tool, or "COMBAT") is described which can search rapidly for highly similar translated genomic sequences, using a stable-marriage procedure with incomplete lists (SMI) as a filter scheme. For example, COMBAT can be applied to a comparative analysis of the human genome with recent bovine genome assemblies, where 84%~95% of the homologous blocks identified by COMBAT can be confirmed by BLASTZ.

An exemplary local alignment procedure which may be used in COMBAT can address several of the challenges described above by implementing the following two stages: (i) generating an index of all overlapping K-mers in translated genomic sequences, where the index can represent the blocks to which a K-mer belongs and which may be used to search efficiently for homologous blocks; and (ii) using SMI procedure to find an optimal one-to-one mapping from a list of multiple local mappings and thereby form a global matching map. COMBAT may not require an assumption of any particular gene order and orientation, it may not require any sophisticated scoring matrix, and it may not have the expensive "extend" stage characteristic of many local alignment programs.

Exemplary embodiment of the present invention relates generally to methods, computer-accessible medium, and systems for comparing a first genome to a second genome. For example, described herein are computer-accessible medium having stored thereon computer executable instructions for comparing a first genome to a second genome. When the executable instructions are executed by a processing arrangement, such instructions configure the processing arrangement to build a first library for the first genome and a second library for the second genome, provide a plurality of matches between elements in the first library common to elements in the second library, rank each match to determine a likelihood of similarity between the common elements in the first and second libraries; and associate matches having a predetermined likelihood, which can result in an alignment of highly similar sequences in the first and second genomes.

Described herein are also methods for comparing a first genome to a second genome, by possibly building a first library for the first genome and a second library for the second genome, providing a plurality of matches between elements in the first library common to elements in the second library, ranking each match to determine a likelihood of similarity between the common elements in the first and second libraries, and associating matches having a predetermined likelihood. For example, the associated matches can result in an alignment of highly similar sequences in the first and second genomes.

Exemplary systems for comparing a first genome to a second genome are also provided. In one exemplary embodiment, such system can include a processing arrangement which, when executed, is configured to build a first library for the first genome and a second library for the second genome, provide a plurality of matches between elements in the first library common to elements in the second library, rank each match to determine a likelihood of similarity between the common elements in the first and second libraries, and associate matches having a predetermined likelihood. For example, the associated matches can result in an alignment of highly similar sequences in the first and second genomes.

These and other objects, features and advantages of the present invention will become apparent upon reading the following detailed description of embodiments of the invention.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 4 is a flow diagram of an exemplary embodiment of a method for comparing a first genome to a second genome in accordance with the present invention.

Figure 1:
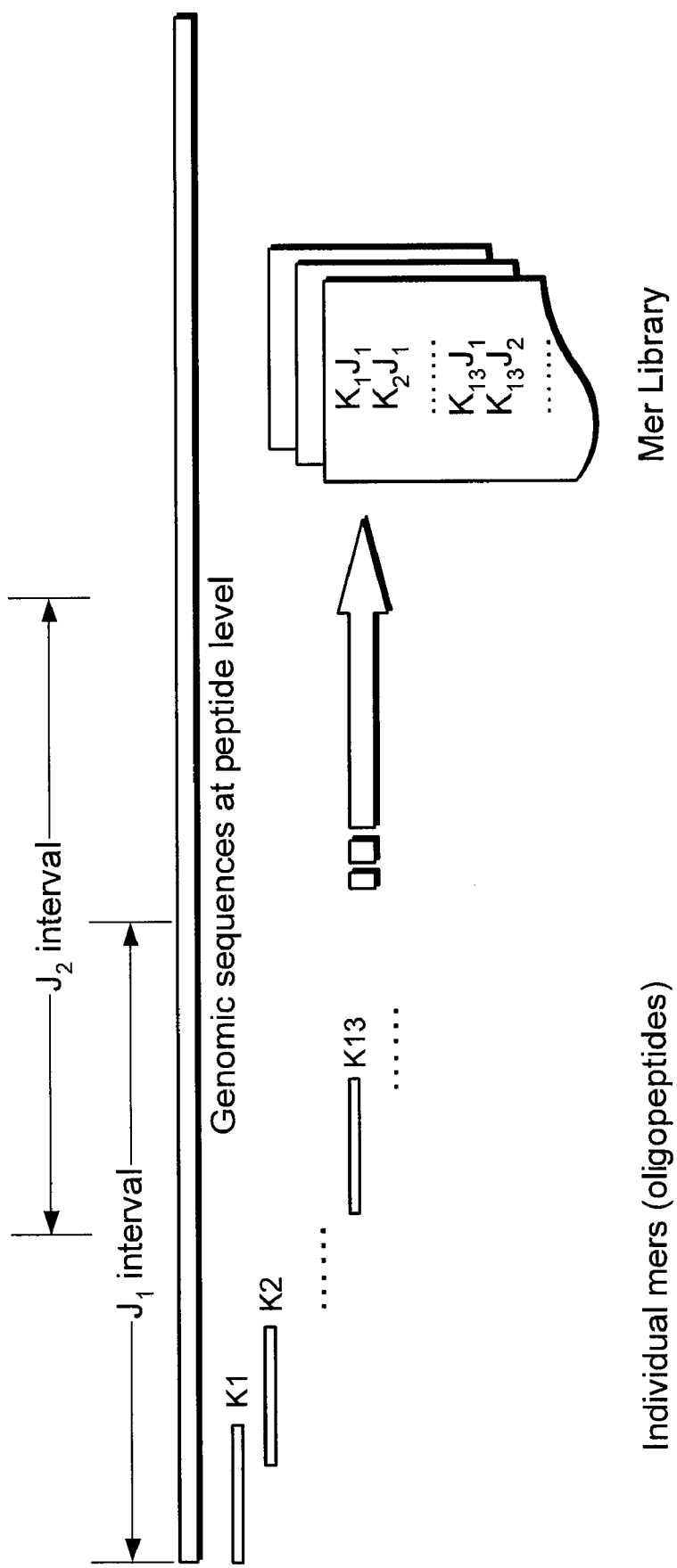
FIG. 1 is a schematic diagram of an exemplary procedure for building a mer library for one genome.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention.

DETAILED DESCRIPTION OF EXEMPLARY EMBODIMENTS OF THE INVENTION

Exemplary embodiments of the present invention can be used to identify protein-encoding regions in genomic sequences using a genome comparison approach. For example, two genomes to be compared can be labeled genome A and genome B. We define some of the terms used below, and present the parameters involved in Table 1. Several parameters which may be used with exemplary embodiments of the present invention are presented in Table 1.

The term J-interval can be understood to include a continuous genomic sequence of length J. Adjacent J-intervals can be spaced J/2 bases apart. The J-interval index can be referred to as a J-index. A Partner Interval Pair (PIP) can occur between a J-interval a in genome A and a J-interval b in genome B (e.g., "PIP (a, b)") if there are more than T K-mers shared by both a and b.

TABLE 1

The involved parameters in COMBAT program

| J | The length of a J-interval |
| K | The K-mer size |
| T | The minimum number of common K-mers required in any PIP |

TABLE 1-continued

The involved parameters in COMBAT program

| S | The actual number of common K-mers in a PIP |
| E, F | The chaining filtering criterion requires that there must be at least F PIPs, each no further than E intervals from each other. |

Exemplary embodiments of the present invention can include the following steps:

1: Build Clean Ordered Mer Libraries

Described herein are methods for building a first library for a first genome, e.g., A, and a second library for a second genome, e.g., B. Genomic sequences of genome A and B can first be translated in all three frames over both forward and reverse orientations and segmented to provide a library of elements for genome A and a library of elements for genome B. For example, after choosing a mer-size K, elements consisting essentially of K-mers can be generated starting at every base position for each genome, ignoring mers in repeats annotated using, e.g., RepeatMasker. The genome being considered can be covered with J-intervals. A "representation of position" which may be attached to each K-mer can represent the index of each J-interval to which it belongs. Only one copy of duplicate K-mers may be retained in each J-interval from the mer library. This technique can provide K-mers that are unique in each interval. The mer library can then be sorted by the mer sequences. Such mer libraries for genome A and genome B may be built separately.

This exemplary procedure for building a mer library is illustrated in FIG. 1. For example, $K_i$ can denote an $i^{th}$ K mer, and $J_j$ can denote an index of the $j^{th}$ J-interval. Most mers (e.g., $K^{13}$) can occur in a region covered by two adjacent J-intervals, so they may appear twice in the mer library.

2: Search for Common Mers/Providing Matches Between Common Elements

The libraries, e.g., clean ordered mer libraries, which may be prepared using the exemplary technique described above, may then be scanned to provide matches between elements in a first library that are common to elements in the second library. Additionally, offsets between the pairs of matching mers found may be computed. When an offset $d_{ij}=A_i-B_j$ exists, it can represent the J-index difference between the i-th mer occurring in genome A and the matching mer in genome B. The J-index of genome B can be easily recovered using $d_{ij}$. This list of mers/offset pairs can then be sorted by their offsets and their J-indexes on genome A. For each J-index of genome A in this list, the number of K-mers that have the same offsets can be counted. Certain intervals may be retained as PIPs if, e.g., the number of common K-mers associated with them is beyond a threshold T as described below.

3: Find One-to-One Correspondence

As a natural result of genome duplications, one region of one genome might match several regions of another genome, e.g., have a likelihood of similarity with several regions of another genome. Often, the single best, orthologous match for each conserved region may appear most significant, and thus should be associated for having a predetermined likelihood. For example, BLASTZ can use the axtBest program to produce the best alignments as described, e.g., in the publication by Schwartz et al.

In exemplary embodiments of the present invention, a "stable marriage" (SM) problem can be applied in large-scale genome comparison as an alignment filter. (Alternatively, a concept of maximum weight matching (MWM) may be used for this task. However, the MWM solver may maximize the cumulative similarity, and thus might not give single best matches for individual regions.) The SM problem is described, e.g., in Gale et al., "College admissions and the stability of marriage," *Am. Math. Monthly*, pages 9-15 (1962). The SM problem can be stated as follows: given two finite equal-sized sets of players, called men and women ($m_i \in$ men, $w_j \in$ women), where each $m_i$ (respectively, $w_j$) ranks $w_j$ (respectively, $m_i$) in strict order forming his/her preference list, find a one-to-one stable match M between the two sexes. M is "stable" if there are no two couples (m, w) and (m', w') in M such that m prefers w' to w and w' prefers m to m'. The so-called "proposal procedure" can solve this problem.

For example, let P={(a, b)} denote the set of all PIPs (a, b) found in step 2, and let X={a|for some b: (a,b)∈P}, and Y={b|for some a: (a,b)∈P}. P can be viewed as a bipartite graph, which is a multiple mapping between two sets of J-indexes. It may then be desired to determine M, a one-to-one stable matching, from P. Since some a in X may generally match to a true subset of Y, this SM problem can become a the relaxed version—e.g., a Stable Marriage Problem with Incomplete Lists (SMI). A preference list for each J-interval in P can be formed as follows:

1. A measure of absolute interval similarity S can be calculated, with $S=\{S_{(a,b)}|(a,b) \in P\}$, where $S_{(a,b)}$ denotes the number of K-mers shared by a PIP (a,b).
2. Relative similarities can be computed subsequently as fractions of the absolute similarities of a best match partner for any J-interval in P. Then, match partners for each J-interval j can be ranked in strict order of their relative similarities to j, thereby forming a preference list for j.

Figure 2:
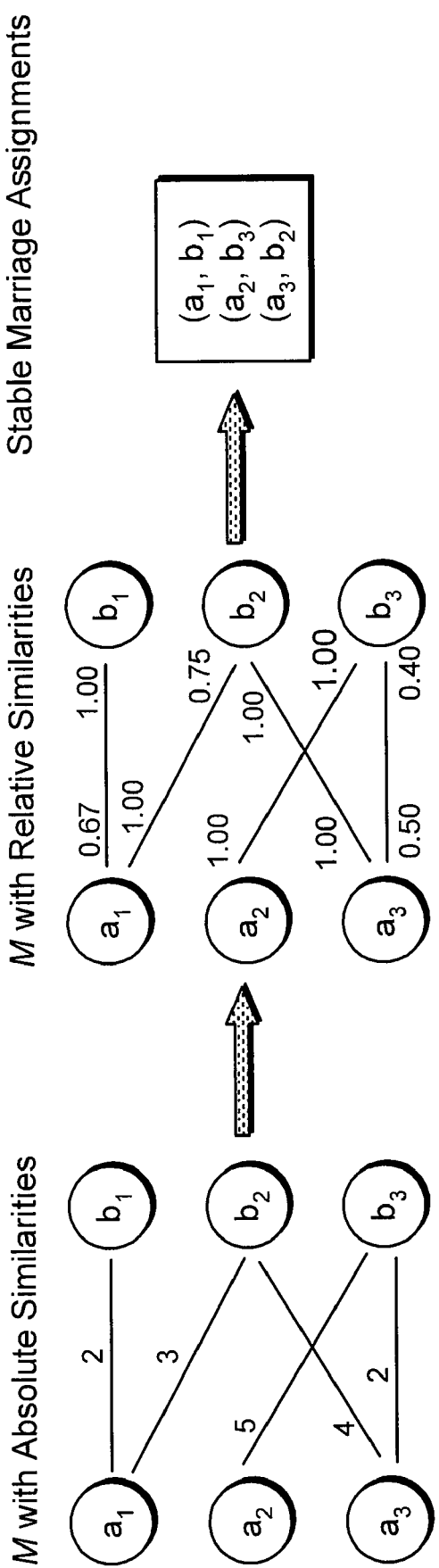
FIG. 2 is a schematic diagram of an exemplary stable marriage procedure.

An example of the stable marriage problem procedure is shown in FIG. 2. Relative similarities can first be computed from absolute similarities in the bipartite graph. An SMI procedure can then be followed to find the stable marriage assignments. For example, $a_1 \sim a_4$ and $b_1 \sim b_4$ can denote the J-indexes on genome A and B, respectively. In multiple mapping M with absolute similarities, the numbers on the edges can represent the number of K-mers shared by the partner intervals. The numbers associated with an edge in the middle panel can represent the relative similarities for a pair of partner intervals.

Each match can be ranked to determine the likelihood of similarity (e.g., relative similarity, R, between the common elements. In the example shown in FIG. 2, $b_2$ can represent the best match for $a_1$, so the value for $R(a_1,b_2)$ can be set equal to 1.00. The relative similarity for the other match partner of $a_1$ can be computed as a fraction of $S(a_1,b_2)$. For example, $$R(a_1, b_1) = \frac{S_{(a_1,b_1)}}{S_{(a_1,b_2)}} = \frac{2}{3} \approx 0.67.$$

Relative similarities may be asymmetric. Under the marriage interpretation, this means that any two match partners may like each other to the different extent. In exemplary embodiments of the present invention, the proposal procedure can be modified and the SMI procedure used, e.g., by COMBAT can be described using the following exemplary code:

```
1.  X={a},Y={b},M={ }. Every a and b has an ordered preference list.
2.  WHILE X is not empty, LOOP
3.    choose an interval a from X
4.    b=the first interval on a's list(If have ties, randomly choose one)
5.    IF a is not on b's preference list, THEN
6.      delete b from a's list;
7.      IF a's preference list is empty, THEN
8.        delete a from X; goto line 2
9.      ELSE goto line 4
10.   ELSE
11.     IF (x, b) is in M for some x in X, THEN
12.       remove (x, b) from M; add x to X;
13.     add (a, b) to M
14.     FOR each successor x (x ranks after a) in b's list, LOOP
15.       delete x from b's list, and b from x's list;
16.     END LOOP
17. END LOOP
18. RETURN M
```

The complexity of this SMI procedure can be $O(n^2)$ in time, and may be linear in space (e.g., n can represent the number of PIPs). The result returned by this procedure can be a list of incomplete one-to-one mapping, e.g., J-intervals in genome A which map to at most one partner in genome B, and vice versa. Further, in order to remove randomly matching PIPs, a chaining procedure can be performed which requires that there must be at least F partner intervals, with each such interval being no further than E intervals from each other. This procedure may not be necessary, e.g., if strict values of J and K are chosen.

Exemplary embodiments of the present invention have been used to compare Human Assembly (hg17, May 2004) and Cow Assembly (bosTau1, September 2004, BCM HGSC Btau_1.0), both of which were obtained from the UCSC Genome Bioinformatics Site. For example, chromosome I from hg17 was aligned with the first 33,000 cow scaffolds using COMBAT. These two sequences are approximately 250 MB in size.

The first sequence can be referred to as chr1, and the second sequence can be referred to as cow1. The resulting alignment maps using different configurations are shown for positive strands in FIG. 3. In this figure, the X-axis represents J-indexes along the chr1 sequence, and the Y-axis represents J-indexes along the cow1 sequence. Maps (1), (2), (4) and (5) of FIG. 3 were obtained using COMBAT, whereas maps (3) and (6) represent transformed results obtained using BLASTZ. Maps (4) and (5) were obtained without using the chaining procedure described above.

Figure 3:
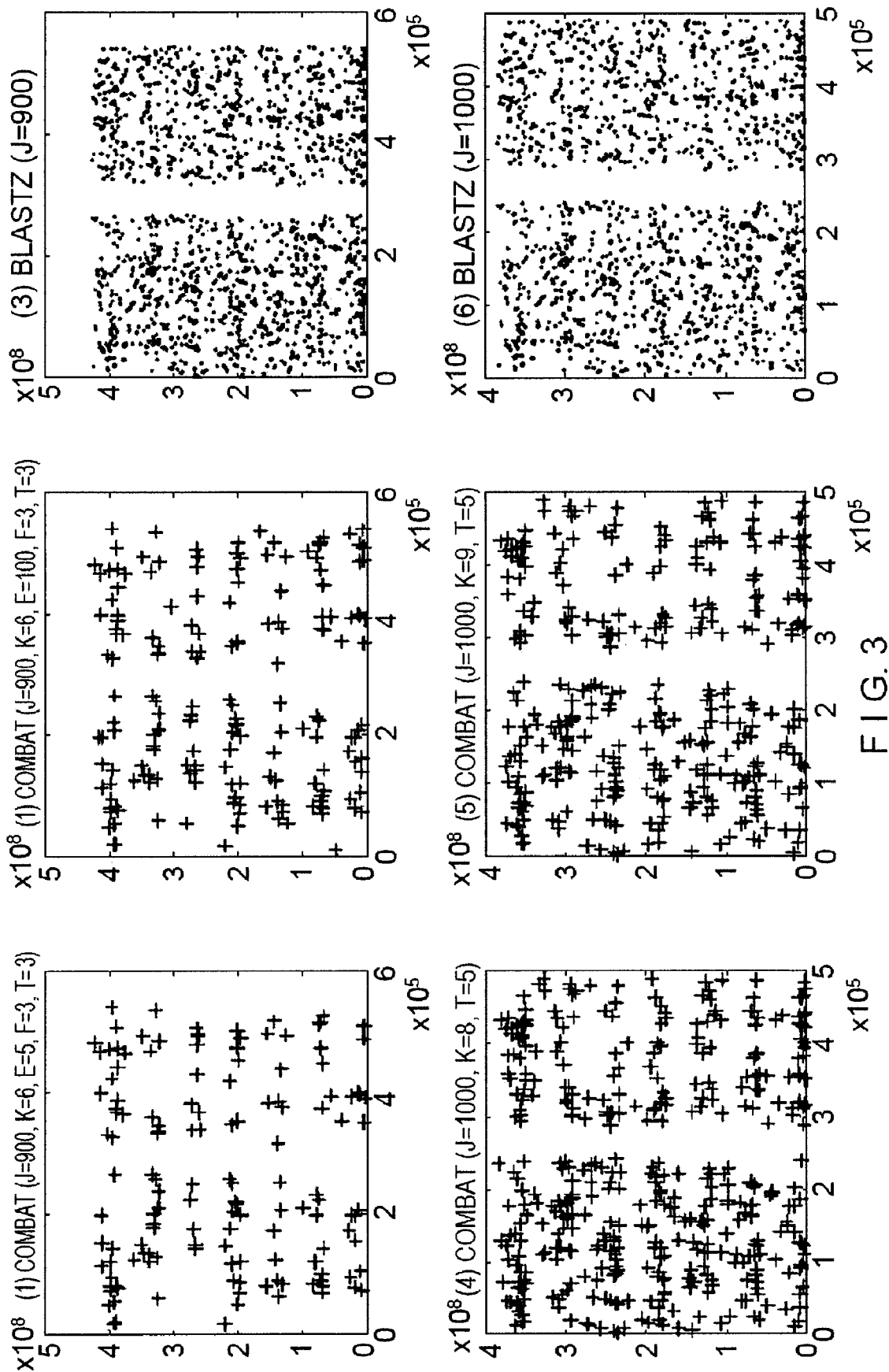
FIG. 3 is a diagram of exemplary alignment maps obtained using COMBAT and BLASTZ.

In maps (1), (2), (4) and (5) of FIG. 3, each plus sign represents the index coordinates of a pair of matching intervals obtained using COMBAT. Maps (3) and (6) were obtained using BLASTZ and filtered by the axtBest program described, e.g., in the publication by Schwartz et al. (These routines were downloaded from the UCSC Genome Bioinformatics Site and transformed to fit the J-intervals context described herein.) In maps (3) and (6), each dot represents index coordinates of the starting positions of two matched regions. The BLASTZ result is transformed twice according to two values of J used.

The chaining criterion used by COMBAT turns out to be relatively insensitive to the value of E used as shown, e.g., in maps (1) and (2) of FIG. 3. The results achieved using exemplary embodiments of the present invention can be evaluated, for example, by testing the appearance of each matching pair of intervals found by COMBAT in the BLASTZ result (transformed by the same J used by COMBAT). For example, a pair of matching J-intervals (a, b) in the COMBAT result can be considered as a true positive case if there exists a pair of matching regions (x, y)(with a and x in genome A, and b and y in genome B) in the BLASTZ result and at least one of the following conditions is satisfied: (i) a is contained in x and b is contained in y; (ii) x is contained in a and y is contained in b; or (iii) the starting positions of a and b are within J.

In map (1) of FIG. 3, 95% of the 625 partner interval pairs found by COMBAT represent true positives as described above. In the other direction, out of 8,389 matching regions in the BLASTZ result, 7% were confirmed by COMBAT. In map (4) of FIG. 3, 84% of 1235 PIPs represent true positives, and they encompass 11% of the BLASTZ results. In map (5) of FIG. 3, 85% of 971 PIPs represent true positives, and they encompass 9% of the BLASTZ results. This high specificity suggests that the exemplary embodiments of the present invention can be used in many applications. The low coverage observed can be related to the expected identification of only highly similar protein-coding regions.

The computational core of the COMBAT procedure was implemented as a C++ program, and exemplary calculations were performed on NYU Bioinformatics Group's cluster of Pentium IV machines with 3 GB memory running RedHat Linux 7.3. Comparing 0.25 Gb of human sequence against 0.24 Gb of cow sequence (e.g., ~1/10 of total genomes) and produce a one-to-one mapping list of highly similar regions required about 23 CPU hours under the configuration shown in map (1) of FIG. 3, and required about 2 CPU hours under the configuration shown in map (4) of FIG. 3. By comparison, BLASTZ required about 481 days of CPU time to align 2.8 Gb of human sequence against 2.5 Gb of mouse sequence on a cluster of 1024 833-Mhz Pentium III computers as described, e.g., in the publication by Schwartz et al.

As an example of error estimation using exemplary embodiments of the present invention, two random J-intervals a in genome A and b in genome B (each of length J over an alphabet of 20 amino acids and 1 stop codon) can be analyzed. These intervals may be considered in one orientation only to simplify the analysis. $P_k$ can denote a probability that there is a common K-mer at any position. If letters are assumed to occur at any given position with equal probability and independency, then $P_k=1/(21)^K$. A positive-valued random variable w can denote the number of common K-mers in a and b. The variable w can be shown to follow a Poisson distribution with parameter $\lambda_w=J^2P_k$. The expectation of a new random variable $\binom{w}{i}$ can be estimated by considering all possible $\binom{J}{i}$ subsets of K-mers from a and counting the probability of each such subset having exact matches with i K-mers in b. This expectation may be expressed as:

$$E\left[\binom{w}{i}\right] = \binom{J}{i}(JP_k)((J-1)P_k)\ldots((J-i+1)P_k) \approx \frac{J^{(i)}}{i!}\left(\frac{J}{21^K}\right)^i \approx \frac{(J^2/21^K)^i}{i!} \quad (1)$$

Using Brun's sieve, the probability that two randomly selected J-intervals from genome A and genome B have exactly m K-mers in common can be expressed as:

$$Pr[w = m] = e^{-(J^2/21^K)}\frac{(J^2/21^K)^m}{m!} \quad (2)$$

Using parameters of this Poisson distribution, a lower threshold can be selected such that two random J-intervals are unlikely (e.g., with probability>1−ε) to have more than $\theta_w$ K-mers in common. Using Chebychev's inequality, a conservative choice for such a threshold can be expressed as:

$$\theta_w = \mu_w + \frac{\sigma_w}{\sqrt{\epsilon}}, \text{ where } \mu_w = \frac{J^2}{21^K}, \sigma_w = \frac{J}{21^{K/2}} \quad (3)$$

As described above, using the one-tailed Chebychev bound can lead to the relationship:

$$Pr(w > \theta_w) = Pr\left(w - \mu_w > \frac{\sigma_w}{\sqrt{\epsilon}}\right) < \epsilon \quad (4)$$

By choosing a very small value of ε (for example, ε≈O(1/G), where G is the genome size), the probability of a false positive can be made sufficiently small.

In the other direction, s can represent a desired similarity value, such that pairs a and b should always be found whenever they have a similarity value of s or higher. The number of observed K-mers shared by a and b can be represented as a random variable v: B(|a∩b|,s) which can have a Binomial distribution with mean μ=|a∩b|s and variance σ²=|a∩b|s(1−s). Using the Chernoff bound, an upper threshold of |a∩b|s/2>Js/4 can be selected to guarantee a probability of success larger than (1−ε), if J is sufficiently large, e.g., Js>16 ln(1/ε). If, for example, ε=1/G, and 16 ln(G)/s<J<<G, the following inequality should be satisfied:

$$\frac{J^2}{21^K} + J\sqrt{\frac{G}{21^K}} < \theta < Js/4 \text{ or } \frac{J}{21^K} + \sqrt{\frac{G}{21^K}} < \theta' < s/4 \quad (5)$$

Because G and s can be determined by the genomes, only K and J need to be selected. Table 2 shows exemplary choices for parameters J and K for provided values of G and s, with ε=1/G. The parameter θ can have the same meaning of the T parameter shown in Table 1. Because ε can be extremely small, the suggested range of θ may be very conservative. Because estimations provided herein may be conservative, exemplary embodiments of the present invention can perform quite well even for suboptimal choices of parameters.

TABLE 2

Exemplary values of parameters J and K.

| s = 0.8 | | s = 0.6 | |
| --- | --- | --- | --- |
| G = 10⁹ | G = 10⁶ | G = 10⁹ | G = 10⁶ |
| J = 1000, | J = 1000, | J = 1000, | J = 1000, |
| K = 8 | K = 6 | K = 9 | K = 6 |
| 162 < θ < 200 | 108 < θ < 200 | 35 < θ < 150 | 108 < θ < 150 |

In summary, many high-speed alignment programs have a fast search stage that uses a heuristic to identify regions likely to be homologous in order to achieve adequate speed when performing comparisons at the scale of whole genomes. Providing a technique for indexing sequences can be very important for an efficient search stage. Exemplary embodiments of the present invention which may use, e.g., COMBAT, can index both genomic sequences. By using an index of intervals instead of genomic positions, the size of the index for a vertebrate genome can be reduced by J-fold, and comparisons can be performed, e.g., on a single CPU machine. Exemplary embodiments of the present invention can be capable of rapidly finding matching regions across vertebrate species working in translated mode. A detailed alignment can then be retrieved by using the standard alignment procedures [e.g., Smith-Waterman, 1970; Needleman-Wunsch, 1981]. Therefore, the challenge of performing complex large-scale genome comparisons can be simplified using exemplary embodiments of the present invention. A one-to-one mapping in a multiple mapping list may also be found by using the SMI procedure.

FIG. 4 shows a flow diagram of an exemplary embodiment of a method for comparing a first genome to a second genome. This exemplary method may be performed by a processing arrangement 100, for example, but not limited to, a computer that includes a microprocessor, and using instructions stored on a computer-accessible medium (RAM, ROM, hard drive, or other storage device). The processing arrangement 100 can receive data 110, which may be the sequence of a first genome and the sequence of a second genome. Then, in step 120, the processing arrangement 100 may prepare a first library comprising elements of the first genome and a second library comprising elements of the second genome. In step 125, the processing arrangement may match elements in the first library with common elements in the second library. In step 130, a stable match between an element in the first library is associated with a stable match in the second library. In step 140, the processing arrangement can determine whether all stable matches have been associated. If not, in step 150, another stable match between an element in the first library and an element in the second library may be associated. If all stable matches have been associated, the exemplary method stops in step 160, whereby the processing arrangement can use a procedure to combine all matches to produce an alignment between the first genome and the second genome.

As also shown in FIG. 4, the processing arrangement 100 may be provided with an input arrangement 105, which may include e.g., a wired network, a wireless network, the internet, an intranet, etc. In addition, the processing arrangement 100 may be provided with an output arrangement 195, which may include, e.g., a wired network, a wireless network, the internet, an intranet, etc.

Figure 5:
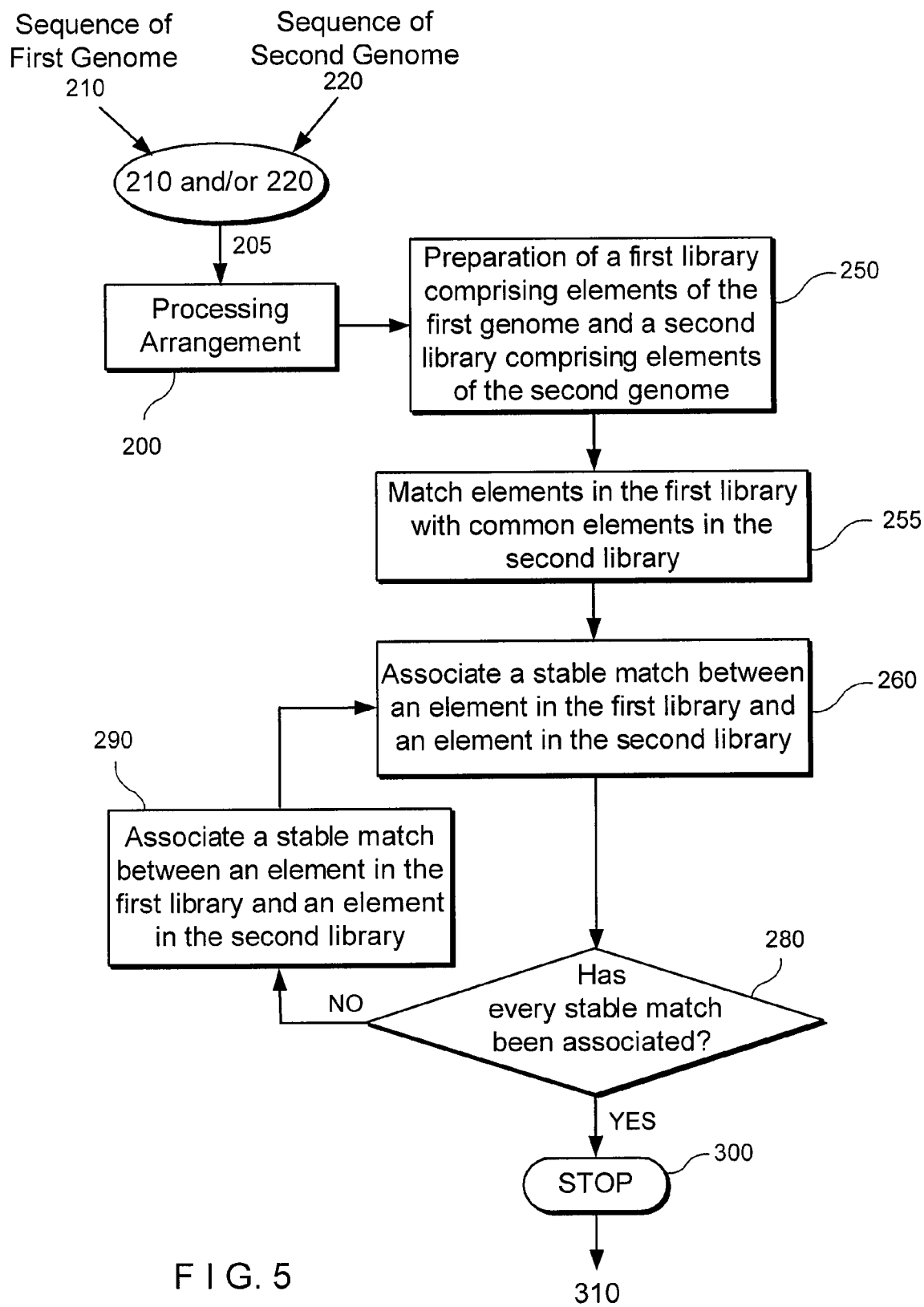
FIG. 5 is a combination of a system diagram and a further flow diagram in accordance with another exemplary embodiment of the present invention.

FIG. 5 shows a diagram of a further exemplary embodiment of a combination of a method and a system for comparing a first genome to a second genome. The exemplary method may be performed by a processing arrangement 200 such as, but not limited to, a computer with a microprocessor, and can be used with instructions provided on a computer accessible medium. For example, the processing arrangement can receive the sequence of a first genome 210 and the sequence of a second genome 220. In step 250, the processing arrangement can prepare a first library comprising elements of the first genome 210 and a second library comprising elements of the second genome 220. In step 155, the processing arrangement may match elements in the first library with common elements in the second library. In step 260, the processing arrangement may associate an element in the first library and an element in the second library if they are a stable match. In step 280, the processing arrangement can determine whether all stable matches have been associated. If not, another stable match may be associated in step 290. If all stable matches have been produced, the exemplary method stops in step 300, whereby the processing arrangement 200 can use a procedure to align the first genome with the second genome.

As shown in FIG. 5, the processing arrangement 200 may be provided with an input arrangement 205, which may include, e.g., a wired network, a wireless network, the internet, an intranet, etc. In addition, the processing arrangement 200 may be provided with an output arrangement 310 which may include, e.g., a wired network, a wireless network, the Internet, an intranet, etc.

Because exemplary embodiments of the present invention can look for exact K-mers matches, they may not be able to identify regions of relatively low similarity. However, such exemplary embodiments can be modified to increase sensitivity. For example, K-mers which include n exactly matching submers $K_1 \sim K_n$ with g number of bases between them (g $\epsilon[0,\alpha]$, where $\alpha$ is a threshold) can be generated. This technique can allow identification of inexact K-mer matches with gaps or mismatches in accordance with exemplary embodiments of the present invention.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. It should be understood that the results of the exemplary embodiments of the present invention can be provided to one or more users, transmitted to one or more computing arrangements, included on a computer-accessible medium (e.g., storage device), a combination thereof, etc. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A non-transitory computer-accessible medium having stored thereon computer executable instructions for comparing a first genome to a second genome which, when the executable instructions are executed by a processing arrangement, configure the processing arrangement to perform procedures comprising:
  (a) generating a first library for the first genome and a second library for the second genome;
  (b) providing a plurality of matches between elements in the first library common to elements in the second library;
  (c) ranking each of the matches to determine a likelihood of similarity between the common elements in the first and second libraries, including:
    (1) setting a first relative similarity value for a match with a highest likelihood of similarity between one element of the first library and common elements of the second library; and
    (2) calculating a relative similarity value as a fraction of the first relative similarity for each other match between the one element of the first library and common elements of the second library; and
  (d) associating the matches having a predetermined likelihood.

2. The computer-accessible medium of claim 1, wherein the first and second libraries are generated separately.

3. The computer-accessible medium of claim 1, wherein the elements are K-mers.

4. The computer-accessible medium of claim 3, wherein each genome is covered with J-intervals, and wherein a representation of position is attached to each K-mer to represent an index of each J-interval to which the K-mer belongs.

5. The computer-accessible medium of claim 4, wherein adjacent J-intervals are spaced J/2 bases apart.

6. The computer-accessible medium of claim 3, wherein the libraries are sorted based on the sequences of the K-mers.

7. The computer-accessible medium of claim 1, wherein matches are provided by determining offsets representing a J-index difference, and wherein at least some of the matches are provided based on the J-index difference.

8. The computer-accessible medium of claim 1, wherein the first relative similarity value equals to 1.00.

9. The computer-accessible medium of claim 1, wherein said associating is performed by a stable marriage procedure.

10. The computer-accessible medium of claim 9, wherein the stable marriage procedure is in quadratic time.

11. The computer-accessible medium of claim 9, wherein the stable marriage procedure is linear in space.

12. The computer-accessible medium of claim 9, wherein the stable marriage procedure results in a list comprising elements in the first library that match at most one element in the second library and elements in the second library that match at most one element in the first library.

13. The computer-accessible medium of claim 1, wherein the providing procedure further comprises performing a chaining procedure.

14. The computer-accessible medium of claim 1, further comprising evaluating each match in a BLASTZ result.

15. The computer-accessible medium of claim 4, wherein the providing procedure further comprises selecting a lower threshold such that two random J-intervals are unlikely to have more than $\theta_\omega$ matched K-mers.

16. The computer-accessible medium of claim 15, wherein the selecting procedure is a conservative choice expressed as $$\theta_\omega = \mu_\omega + \frac{\sigma_\omega}{\sqrt{\epsilon}}, \text{ where } \mu_\omega = \frac{J^2}{21^K}, \sigma_\omega = \frac{J}{21^{\frac{K}{2}}}.$$

17. The computer-accessible medium of claim 1, wherein the associated matches are in an alignment of significantly similar sequences in the first and second genomes.

18. A method for comparing a first genome to a second genome, comprising:
(a) generating a first library for the first genome and a second library for the second genome;
(b) providing a plurality of matches between elements in the first library common to elements in the second library;
(c) ranking, with a hardware processing arrangement, each of the matches to determine a likelihood of similarity between the common elements in the first and second libraries including:
(1) setting a first relative similarity value for a match with a highest likelihood of similarity between one element of the first library and common elements of the second library; and
(2) calculating, with the electronic processor, a relative similarity value as a fraction of the first relative similarity value for each other match between the one element of the first library and common elements of the second library; and
(d) associating the matches having a predetermined likelihood.

19. The method of claim 1, wherein the associated, matches are in an alignment of significantly similar sequences in the first and second genomes.

20. A system for comparing a first genome to a second genome, comprising:

a hardware processing arrangement configured to perform procedures comprising:
(a) generating a first library for the first genome and a second library for the second genome;
(b) providing a plurality of matches between elements in the first library common to elements in the second library;
(c) ranking each match to determine a likelihood of similarity between the common elements in the first and second libraries, including:
(1) setting a first relative similarity value for a match with a highest likelihood of similarity between one element of the first library and common elements of the second library; and
(2) calculating a relative similarity value as a fraction of the first relative similarity value for each other match between the one element of the first library and common elements of the second library; and
(d) associating the matches having a predetermined likelihood.

21. The system of claim 20, wherein the elements are K-mers.

22. The system of claim 21, wherein each genome is covered with J-intervals, and wherein a representation of position is attached to each K-mer to represent an index of each J-interval to which the K-mer belongs.

23. The system of claim 20, wherein the associated matches are in an alignment of significantly similar sequences in the first and second genomes.

24. A non-transitory computer-accessible medium having stored thereon computer executable instructions for comparing a first genome to a second genome which, when the executable instructions are executed by a processing arrangement, configure the processing arrangement to perform procedures comprising:
(a) generating a first library for the first genome and a second library for the second genome;
(b) providing a plurality of matches between elements in the first library common to elements in the second library by performing a chaining procedure;
(c) ranking each of the matches to determine a likelihood of similarity between the common elements in the first and second libraries; and
(d) associating the matches having a predetermined likelihood.

25. The computer-accessible medium of claim 24, wherein the first and second libraries are generated separately.

26. The computer-accessible medium of claim 24, wherein the elements are K-mers.

27. The computer-accessible medium of claim 26, wherein the libraries are sorted based on the sequences of the K-mers.

28. The computer-accessible medium of claim 26, wherein each genome is covered with J-intervals, and wherein a representation of position is attached to each K-mer to represent an index of each J-interval to which the K-mer belongs.

29. The computer-accessible medium of claim 28, wherein adjacent J-intervals are spaced J/2 bases apart.

30. The computer-accessible medium of claim 24, wherein the providing procedure further comprises selecting a lower threshold such that two random J-intervals are unlikely to have more than $\theta_\omega$ matched K-mers.

31. The computer-accessible medium of claim 30, wherein the selecting procedure is a conservative choice expressed as $$\theta_\omega = \mu_\omega + \frac{\sigma_\omega}{\sqrt{\epsilon}}, \text{ where } \mu_\omega = \frac{J^2}{21^K}, \sigma_\omega = \frac{J}{21^{\frac{K}{2}}}.$$

32. The computer-accessible medium of claim 24, wherein matches are provided by determining offsets representing a J-index difference, and wherein at least some of the matches are provided based on the J-index difference.

33. The computer-accessible medium according to claim 24, wherein the ranking procedure comprises:
   (1) setting a first relative similarity value for a match with a highest likelihood of similarity between one element of the first library and common elements of the second library; and
   (2) calculating a relative similarity value as a fraction of the first relative similarity for each other match between the one element of the first library and common elements of the second library.

34. A method for comparing a first genome to a second genome, comprising:
   (a) generating a first library for the first genome and a second library for the second genome;
   (b) providing a plurality of matches between elements in the first library common to elements in the second library by performing a chaining procedure;
   (c) ranking with a hardware processing arrangement each of the matches to determine a likelihood of similarity between the common elements in the first and second libraries; and
   (d) associating the matches having a predetermined likelihood.

35. A non-transitory computer-accessible medium having stored thereon computer executable instructions for comparing a first genome to a second genome which, when the executable instructions are executed by a processing arrangement, configure the processing arrangement to perform procedures comprising:
   (a) generating a first library for the first genome and a second library for the second genome;
   (b) providing a plurality of matches between K-mers in the first library common to K-mers in the second library;
   (c) ranking each of the matches to determine a likelihood of similarity between the common elements in the first and second libraries; and
   (d) associating the matches having a predetermined likelihood, wherein each genome is covered with J-intervals, and wherein a representation of position is attached to each K-mer to represent an index of each J-interval to which the K-mer belongs.

36. The computer-accessible medium of claim 35, wherein adjacent J-intervals are spaced J/2 bases apart.

37. The computer-accessible medium of claim 35, wherein the providing step further comprises selecting a lower threshold such that two random J-intervals are unlikely to have more than $\theta_\omega$ matched K-mers.

38. The computer-accessible medium of claim 37, wherein the selecting procedure is a conservative choice expressed as $$\theta_\omega = \mu_\omega + \frac{\sigma_\omega}{\sqrt{\epsilon}}, \text{ where } \mu_\omega = \frac{J^2}{21^K}, \sigma_\omega = \frac{J}{21^{\frac{K}{2}}}.$$

39. The computer-accessible medium according to claim 35, wherein the ranking procedure comprises:
   (1) setting a first relative similarity value for a match with a highest likelihood of similarity between one element of the first library and common elements of the second library; and
   (2) calculating a relative similarity value as a fraction of the first relative similarity for each other match between the one element of the first library and common elements of the second library.

40. The computer-accessible medium of claim 35, wherein the providing procedure further comprises performing a chaining procedure.

41. A method for comparing a first genome to a second genome, comprising:
   (a) generating a first library for the first genome and a second library for the second genome;
   (b) providing a plurality of matches between K-mers in the first library common to K-mers in the second library;
   (c) ranking with a hardware processing arrangement each of the matches to determine a likelihood of similarity between the common elements in the first and second libraries; and
   (d) associating the matches having a predetermined likelihood, wherein each genome is covered with J-intervals, and wherein a representation of position is attached to each K-mer to represent an index of each J-interval to which the K-mer belongs.

* * * * *